US012678136B2

(12) United States Patent
Hatlan et al.

(10) Patent No.: US 12,678,136 B2
(45) Date of Patent: ***Jul. 14, 2026

(54) WEARABLE PORTABLE ULTRASOUND PROBE

(71) Applicant: Sonivate Medical, Inc., Portland, OR (US)

(72) Inventors: James T. Hatlan, Portland, OR (US); Austen Angell, Portland, OR (US); William McDonough, Portland, OR (US)

(73) Assignee: Sonivate Medical, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 18/623,792

(22) Filed: Apr. 1, 2024

(65) Prior Publication Data

US 2024/0260939 A1     Aug. 8, 2024

Related U.S. Application Data

(63) Continuation of application No. 17/125,662, filed on Dec. 17, 2020, now Pat. No. 11,944,493, and a continuation-in-part of application No. 16/272,146, filed on Feb. 11, 2019, and a continuation-in-part of application No. 16/272,181, filed on Feb. 11, 2019, now abandoned.

(51) Int. Cl.
*A61B 8/00* (2006.01)

(52) U.S. Cl.
CPC .......... *A61B 8/4455* (2013.01); *A61B 8/4427* (2013.01); *A61B 8/4477* (2013.01); *A61B 8/4488* (2013.01)

(58) Field of Classification Search
CPC ... A61B 8/4455; A61B 8/4427; A61B 8/4477; A61B 8/4488
See application file for complete search history.

*Primary Examiner* — Alexei Bykhovski
(74) *Attorney, Agent, or Firm* — K&L Gates LLP; Brian J. Novak; Dennis Majewski

(57) ABSTRACT

Disclosed are wearable ultrasound probes for use in trauma triage and assessment. The probes include a housing having a dorsal side and a palmar side, a proximal end and a distal end, and a longitudinal axis extending therebetween. The proximal end comprises a finger-receiving aperture that is configured to form a sleeve including a tubular wall member formed from an elastomeric material and defining an inner lumen. A portion of the tubular wall member is configured to extend or project into the inner lumen to form a deformable gripping member for gripping a finger. The probes also include at least one ultrasound array disposed at the distal end or adjacent to the distal end.

20 Claims, 13 Drawing Sheets

Model A

Model B

Model C

Model D

Model E

WEARABLE PORTABLE ULTRASOUND PROBE

PRIORITY CLAIM

This application is a continuation application of U.S. Non-Provisional patent application Ser. No. 17/125,662, filed Dec. 17, 2020, now U.S. Pat. No. 11,944,493, which is a continuation-in-part of U.S. Non-Provisional patent application Ser. No. 16/272,146, filed Feb. 11, 2019, and is a continuation-in-part of U.S. Non-Provisional patent application Ser. No. 16/272,181, filed Feb. 11, 2019, entitled Graphical User Interface for Ultrasound System, the entire disclosures of which are hereby incorporated by reference.

STATEMENT OF GOVERNMENT SUPPORT

This invention was made with government support under contract number W81XWH-17-C-0024 awarded by The United States Army Medical Research and Material Command, and W81XWH-15-C-001 awarded by the Defense Health Program, United States Department of Defense. The government has certain rights in the invention.

CROSS REFERENCE TO RELATED APPLICATIONS

This application is related to U.S. Provisional Patent Applications 62/634,132 entitled Wearable Ultrasound Probe and System, and 62/634,101, entitled Graphical User Interface for Ultrasound System, both of which are hereby incorporated by reference in their entireties for all purposes.

TECHNICAL FIELD

Embodiments relate to medical imaging technologies, and more specifically, to portable ultrasound technologies

BACKGROUND

Many trauma patients have injuries that are not apparent on the initial physical examination. For example, patients with penetrating cardiac trauma, blunt or penetrating abdominal trauma, or chest trauma may have sustained life threatening injuries without much external blood loss. Without rapid assessment of internal bleeding, these injuries may be overlooked in the initial assessment of a patient, and appropriate treatment may be delayed.

Ultrasound imaging can be used to identify the accumulation of intraperitoneal or pericardia! free fluid and/or collapsed lung in trauma patients. Emergency physicians in the United States began using bedside or Point of Care (POC) ultrasound imaging of trauma patients in the 1980's. Ultrasound imaging has since become the initial imaging test of choice for trauma care in the United States and is part of the Advanced Trauma Life Support protocol developed by the American College of Surgeons.

POC ultrasound imaging of trauma patients consists of either the Focused Assessment using Sonography in Trauma (FAST) exam or the extended FAST exam (eFAST).

Ultrasonic eFAST examination provides a universally-accepted triage and trauma assessment tool. The eFAST exam is quicker and less expensive compared to computative tomography (CT) imaging, and thus can provide vital information without the time delay caused by radiographs or CT imaging. An experienced user can conduct an eFAST examination in five minutes.

An eFAST examination involves seven to nine separate scans. Each scan requires the operator to move the probe to a different area of the body, adjust the operation of the probe, and acquire and interpret scans of the relevant physiology. Some scans should be performed with an entirely different probe. The eFAST exam typically requires two probes: one with a low frequency ultrasound array, i.e., 1-5 MHZ, for deep abdominal scans, and a probe with a high frequency ultrasound array, i.e., 5-13 MHZ, for shallow scans, such as to detect pneumothorax or collapsed lung. Low frequency phased arrays have the additional advantage of being able to minimize visual interference from ribs, and high frequency arrays provide greater image clarity for near field viewing as described further below. For many portable or cart-based ultrasound systems, an operator must disconnect one probe, connect another probe, adjust the system to accommodate the change in probe, position the probe at the relevant area of the body, and acquire and interpret the image. The majority of hand-held ultrasound systems requires two different probes to conduct an eFAST examination—one of each high and low frequency.

The number of scans and sequence in which eFAST scans are performed is subject to the personal preference of the clinician performing the scan, informed by the clinical impression of the patient. A clinician who suspects collapses lung or pneumothorax will likely begin the examination with thoracic scans, while a clinician who suspects abdominal trauma may begin the examination in the pelvic region.

Battlefield medics have an urgent need for a fast and effective way to triage individuals who have sustained traumatic injuries. The eFAST exam would provide battlefield medics with an important triage tool. However, battlefield medics are typically inexperienced or novice ultrasound operators. Conventional equipment is designed for the use of operators with extensive experience and training in the use of ultrasound. It provides little structure or guidance in order to afford the operator with the opportunity to conduct the test in accordance with his or her preferences and impressions of the patient as informed by clinical judgment. This lack of structure or guidance does not provide an inexperienced operator with necessary support. Novice users and even those who use ultrasound infrequently typically find conventional controls and/or user interfaces to be counterintuitive and unhelpful. This lack of structure or guidance is not a problem in the context of a clinic or hospital, where personnel having specialized training and experience operating ultrasound systems are readily available. But battlefield medics must triage patients with the skills they have, often under exceptionally stressful circumstances.

Bulky equipment cannot be carried into the field without compromising the mobility and safety of the operator. Switching back and forth between probes and adjusting the machine accordingly make additional demands on a medic who is fully occupied with triaging and caring for patients.

Emergency responders who are not battlefield medics also must accurately and rapidly triage patients under extraordinarily demanding and difficult circumstances including but limited to mass shootings, natural disasters, etc. eFast examinations would also be of value to emergency responders, but many of the same problems with conventional systems make their use by emergency responders in the field impractical.

DETAILED DESCRIPTION OF DISCLOSED EMBODIMENTS

Figure 1:
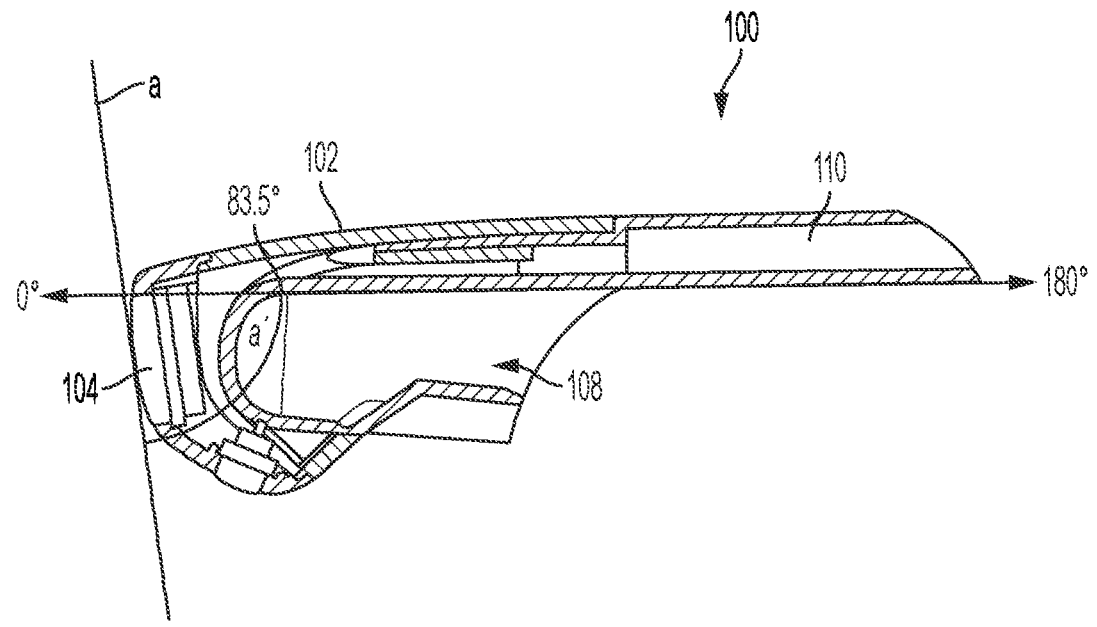
FIG. 1 is a lateral sectional view of an ultrasound probe that can be optionally worn on a finger, illustrating the angle between the longitudinal axis and the first array, in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments. The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact.

However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (Band C), or (A, Band C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Embodiments herein provide wearable, finger-mounted ultrasound probes and small, portable ultrasound systems that may be used for diagnosing trauma, for example using the eFAST examination. Conventional ultrasound systems include two components: a probe and a workstation. The probe contains the array or arrays of ultrasound transducer elements that convert electrical impulses to ultrasonic energy and vice-versa. Either the probe or the workstation includes front end functions, such as beam forming or creation of electrical impulses which are converted to and from ultrasonic energy by the array. The workstation contains a computational back-end, which processes the image data generated by the front end, a display, and a user interface including a keyboard or other means of input of user control.

These components are typically fairly large, which makes them unsuitable for use in the field and difficult to move from area to area within a field hospital, aid station, or other emergency medical setting. Even portable systems typically are no less than laptop computer-sized, which is still prohibitively large for field environments, where minimizing the gear a medic or responder must carry is critical. Additionally, emergency medical technicians, search and rescue professionals, and medics who must operate in conditions impacted by combat or natural disasters have urgent needs for medical imaging in order to better assess the nature and extent of injuries, but conventional ultrasound technology is too complex or difficult to carry and deploy quickly.

Additionally, in a traditional clinical setting, multiple personnel typically are available to perform different roles, including caring for, stabilizing, and treating the patient and performing diagnostic activities including operating an ultrasound system, obtaining images, and interpreting those images. In such a setting, personnel are generally available who have received extensive training and/or have extensive experience with ultrasound, and ultrasound examinations are generally conducted by such individuals. And because other personnel are available to perform other roles, ultrasound operators are able to focus on performing ultrasound examinations.

In contrast, a first responder or military field medic must examine, support, triage, and stabilize patients in a potentially challenging environment. They do not generally have the opportunity to develop extensive expertise, training, and experience in operating an ultrasound system, obtaining images, or understanding and interpreting ultrasound images. Nor do they generally have the ability to focus exclusively on the conduct of an ultrasound examination, as other tasks as well as the challenges of their settings compete for their attention.

In order to be useable in an emergency setting outside of a conventional hospital, a system must be compact enough to be easily transported, and it must be as simple and intuitive to use as possible in order to minimize demands on the user's attention and cognitive capacity, yet it must provide sufficient support to enable a user with a relative lack of specialized skills to effectively and efficiently conduct the examination.

To address these issues, the disclosed systems may include an ultrasound probe that emits and receives ultrasonic energy, and a portable component that is electrically connected with the ultrasound probe to provide power and ultrasound beamforming technology to the ultrasound probe, and to a tablet, mobile phone, or other small wireless computing device. These components may be interconnected by USB cable or other means. In various embodiments, the disclosed systems also may include at least one user interface, such as a GUI, that may be displayed on a tablet, mobile phone, or other small wireless computing device, and at least one set of instructions stored on and executable by the tablet, phone, portable component, or other small wireless computing device. In use, execution of the instructions by the tablet, mobile phone, or other small wireless computing device may cause the portable component and in turn the ultrasound probe to emit and receive ultrasonic energy in accordance with one or more sets of preset parameters, and the user interface may allow a user to select one of the sets of preset parameters to carry out one or more steps of the eFAST exam. In various embodiments, the mobile phone and/or tablet may include some processing requirements that the beamformer and/or portable component cannot perform. In those embodiments, some processing of the data transmitted from the portable component may be performed by software on the tablet and or mobile phone.

In various embodiments, the portable systems may communicate through a USB cable, standard wireless or limited, ultra-wide-band wireless (UWB) to a tablet, phone, or other portable wireless device, which functions as the display and user interface. In various embodiments, the probes may include a first array that includes a low frequency phased array, and a second array that includes a high frequency linear array. In other embodiments, the probes include only the high frequency linear array. In various embodiments, the disclosed systems and probes may allow a field medic or other operator to use a single, compact probe to carry out all of the steps of an eFAST exam, which may reduce the amount of equipment that must be carried with or by the operator. Additionally, the system may include a tablet- or mobile phone-based graphical user interface (GUI) that may direct a user with little training in ultrasonography to carry out an eFAST exam effectively in a battlefield environment. In various embodiments, the array or arrays are positioned on the probe in such a way as to maximize ergonomics for the user. If the probe has more than one array, the arrays are positioned with respect to one another in an orientation that minimizes the change in hand position required to switch between arrays, while also providing sufficient separation between the first and second arrays to make it easy for an inexperienced user to track which array is being used (and consequently, to be able to easily interpret the resulting ultrasound images). Disclosed herein are probes having arrays positioned with respect to one another at angles that satisfy these conditions. In other embodiments, the probe contains a single array which is oriented with respect to the housing to maximize user ergonomics. Such probes may be wearable and intended to mount on a finger, having receptacles for the accommodation of a user's finger.

However, these angles are also applicable to probes that are not worn or finger-mounted, especially small, lightweight hand-held probes.

FIG. 1 is a lateral sectional view of an ultrasound probe, illustrating the angle between the longitudinal axis and the first array, in accordance with various embodiments. As illustrated, the probe 100 may include a housing 102 having a top side (as illustrated in FIG. 1) and a bottom side (as illustrated in FIG. 1), a proximal end (right, as illustrated in FIG. 1) and a distal end (left, as illustrated in FIG. 1), and a longitudinal axis extending therebetween and generally aligning with the longitudinal axis of the operator's finger when in use (labeled 0-180 in FIG. 1). For the purpose of this disclosure, the longitudinal axis is measured along the bottom edge of the strain relief 110, which rests on the dorsal surface of the user's finger during use in a finger-mounted probe.

The proximal end of the housing (closest to the operator in use) may optionally include a finger-receiving aperture 108 so that the housing may be slid onto a user's finger. If the probe has two arrays, the first ultrasound array 104 may be disposed at the distal end of the housing, near the user's fingertip. The axis of the first array 104 is illustrated by line a in FIG. 1. As illustrated in FIG. 1, in various embodiments, the angle a' between the longitudinal axis and the axis a of the first array 104 may be about 60-105 degrees, such as about 65-100 degrees, about 70-95 degrees, about 75-90 degrees, about 80-85 degrees, or about 83-84 degrees relative to the longitudinal axis.

Figure 2:
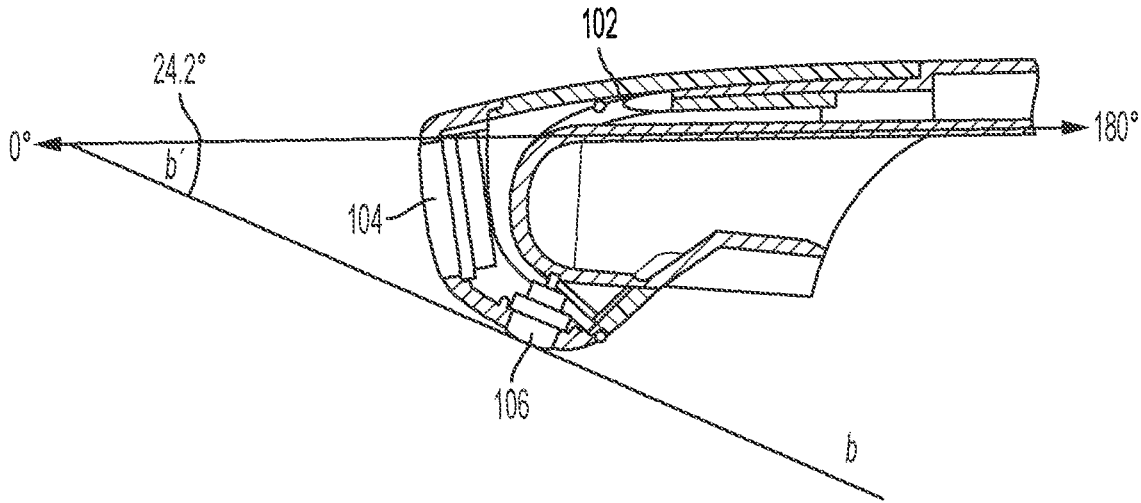
FIG. 2 is a lateral sectional view of the ultrasound probe of FIG. 1, illustrating the angle b' between the longitudinal axis and the axis b of the second array, in accordance with various embodiments.

FIG. 2 is a lateral sectional view of the finger-mounted ultrasound probe of FIG. 1, illustrating the angle b' between the longitudinal axis and the axis b of the high frequency linear array 106, in accordance with various embodiments. As illustrated in FIG. 2, the high frequency linear array 106 may be disposed near the distal end of the housing 102. In various embodiments, the angle b' between the longitudinal axis and the axis b of the high frequency linear array 106 may be about 10-50 degrees, such as about 15-45 degrees, about 20-40 degrees, about 20-30 degrees, or about 24-25 degrees relative to the longitudinal axis.

Figures 3, 4:
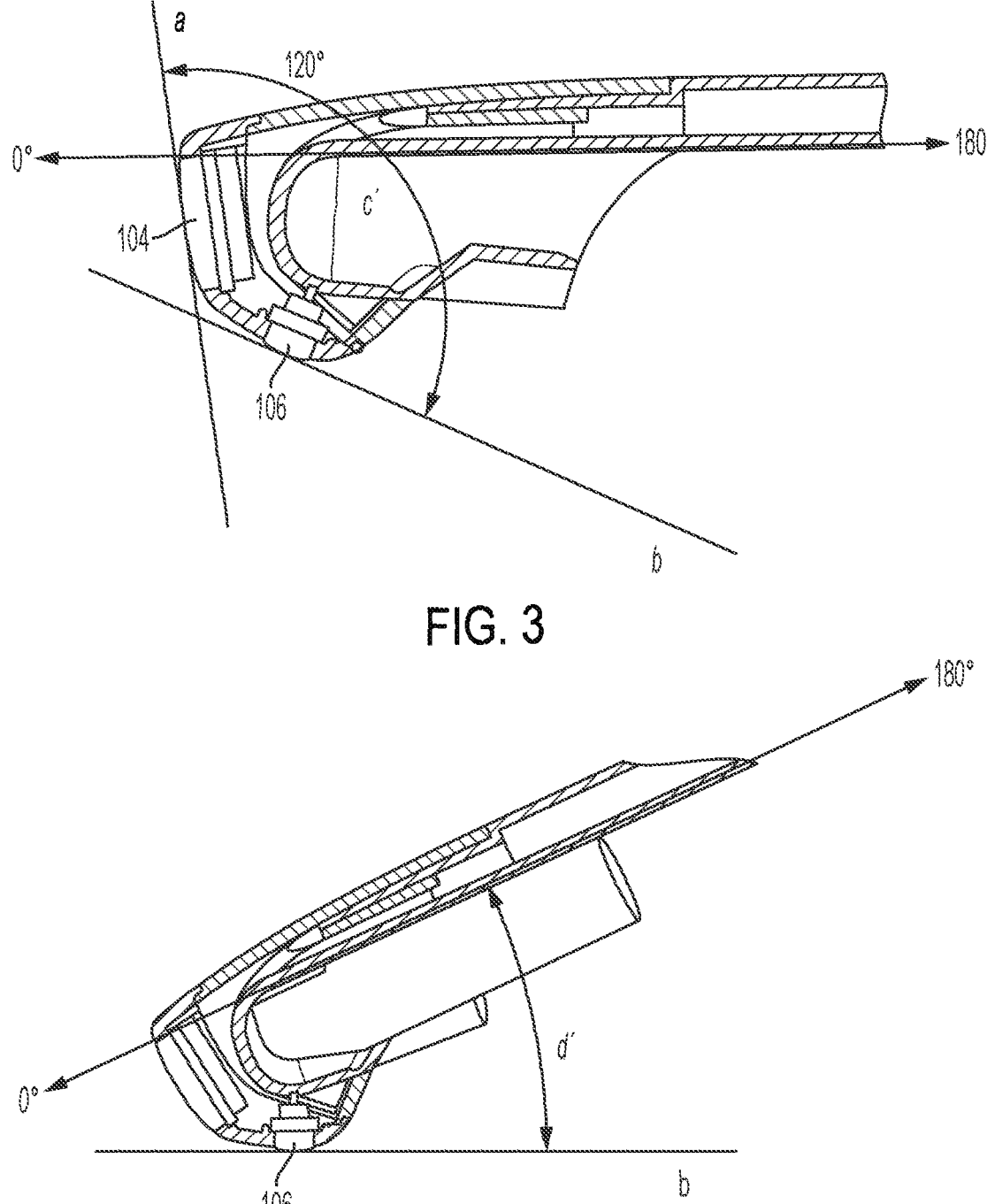
FIG. 3 is a lateral sectional view of the ultrasound probe of FIG. 1, illustrating the angle c' between the axis a of the first array and the axis b of the second array, in accordance with various embodiments.
FIG. 4 illustrates the angle of the ultrasound probe of FIG. 1 when the second array is being used, in accordance with various embodiments.

FIG. 3 is a lateral sectional view of the finger-mounted ultrasound probe of FIG. 1, illustrating the angle c' between the axis a of the first array 104 and the axis b of the second array 106, in accordance with various embodiments. As illustrated in FIG. 3, in various embodiments, the angle c' between the axis a of the first array 104 and the axis b of the second array 106 may be about 105-155 degrees, such as about 110-145 degrees, about 115-135 degrees, about 115-125 degrees, or about 120 degrees.

Where two arrays are present, the separation between the first array and the second array needs to be large enough for the user to easily distinguish between the two arrays during use, but the hand angle also needs to be comfortable during use so as not to cause strain on the hand and wrist of the user. The angles and ranges defined above define a unique set of values that meet both of these conflicting needs. In various embodiments, the first and second arrays may be oriented parallel to each other. In some embodiments, both the first and second arrays may be transverse relative to the longitudinal axis.

Figures 5, 6:
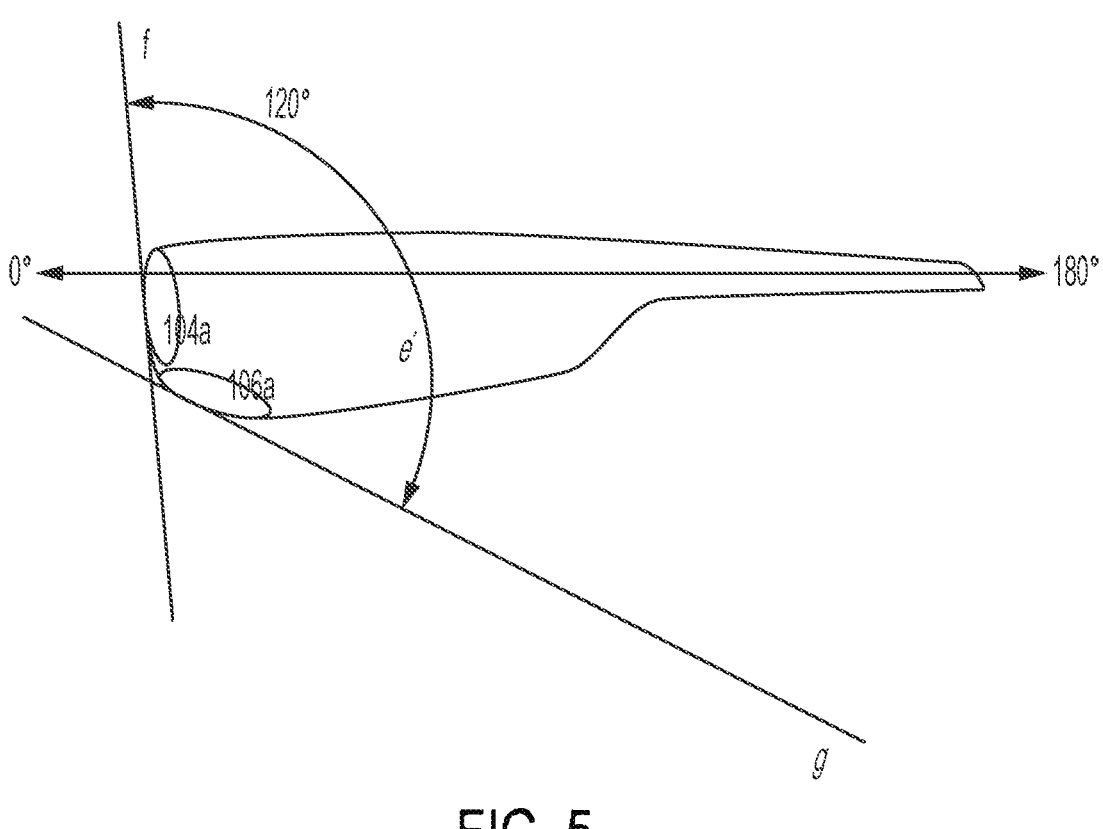
FIG. 5 is a lateral sectional view of one embodiment of a dual-array ultrasound probe as disclosed herein, illustrating the angle e' between the axis f of the first array and the axis g of the second array, in accordance with various embodiments.
FIG. 6 is a lateral sectional view of the ultrasound probe of FIG. 5, illustrating the angle h' between the longitudinal axis and the axis g of the second array, in accordance with various embodiments.

FIG. 5 is a lateral sectional view of a dual-array probe in accordance with various embodiments, illustrating the angle e' between the axis f of the first array 104a and the axis g of the second array 106a, in accordance with various embodiments. As illustrated in FIG. 5, in various embodiments, the angle e' between the axis f of the first array 104a and the axis f of the second array 106a may be about 105-155 degrees, such as about 110-145 degrees, about 115-135 degrees, about 115-125 degrees, or about 120 degrees.

FIG. 6 is a lateral sectional view of an ultrasound probe in accordance with various embodiments illustrating the angle h' between the longitudinal axis and the axis g of the high frequency linear array 106a, in accordance with various embodiments. In various embodiments, the angle h' between the longitudinal axis and the axis g of the high frequency linear array 106a may be about 10-50 degrees, such as about 15-45 degrees, about 20-40 degrees, about 20-30 degrees, or about 24-25 degrees relative to the longitudinal axis. In accordance with certain embodiments, the linear array 106 or 106a needs to lie flat on the patient for performing scans such as the pneumothorax portion of the eFAST exam, as well as for other applications like line placements. However, if the angle h' is too shallow the user's ability to apply appropriate pressure with the probe may be compromised. In these embodiments, the angle between the longitudinal axis and the axis of the array may be about 10-50 degrees, such as about 15-40 degrees, about 20-30 degrees, or about 24 degrees relative to the longitudinal axis.

In general, probes of various shapes and architectures permit varying fields of views. For example, a curved linear array with relatively small radius of curvature permits imaging in the near field of the probe over a wide field of view. A phased array permits imaging over a wide field of view at some distance from the array, while allowing imaging through a narrow access. A linear array permits imaging over a narrower field of view, but provides good imaging of structures near the surface of the array.

The presently disclosed dual-array probes include a phased array as the first array 104 or 104a which is positioned at the distal end of the housing, and a linear array as the second array 106 or 106a which is positioned just proximal to the first array 104 or 104a. This architecture allows an operator to carry out the bulk of the eFAST exam using the first array, which is positioned at the tip of the probe and angled slightly toward the bottom surface (e.g., angled slightly toward the pad of the finger tip when the probe is worn) to optimize ease of use and to afford an intuitive, ergonomic hand position during the examination. The second array, which is located adjacent to the first array, may be accessed by the operator with a slight change in hand angle for the pneumothorax-detection portions of the eFAST exam. The angle between the first and second arrays is optimized so that a relatively untrained operator may easily switch between arrays without confusion, while still maintaining an ergonomic hand position. The two arrays may be oriented so that they have the same scan plane, which is preferably transverse to the user's finger. Having both arrays oriented in the same scan plane means that changing the array does not change the scan plane, which makes switching between arrays more intuitive for novice or inexperienced users. If the user desires to a scan plane that is transverse to the user's finger, he or she can use the array located at the tip of the finger, and can rotate his or her finger to rotate the array, a movement which is intuitive. Alternatively, he or she can hold the probe in his or her hand and rotate it.

In various embodiments, the first and second arrays are oriented in a transverse direction, which permits a user to begin the examination with his or her hand transverse to the length of the patient's torso, which is a more natural position than parallel to the length of the patient's torso. Additionally, the combination of a straight linear array and a phased array allows the probe head profile to be minimized.

In various embodiments, the disclosed probes are particularly advantageous for use by field medics who lack specialized ultrasound expertise because the ergonomic form of the probe leverages innate hand-eye coordination to simplify use and training. The parallel transverse orientation of the two arrays helps prevent confusion in an inexperienced user, which is particularly important in high-stress settings, such as the battlefield. Additionally, the disclosed probes help keep a user's hand and arm available for other uses.

In various embodiments, the first and second arrays of the disclosed probes may be electrically interconnected with a cable on a dorsal aspect of the probe. As illustrated in FIG. 1, a strain relief 110 may be provided to house and protect the cable. The cable may be made of flex circuit or any other electrically conductive or connective material that may be employed to electrically couple to the first and second arrays 104, 106.

Figure 7:
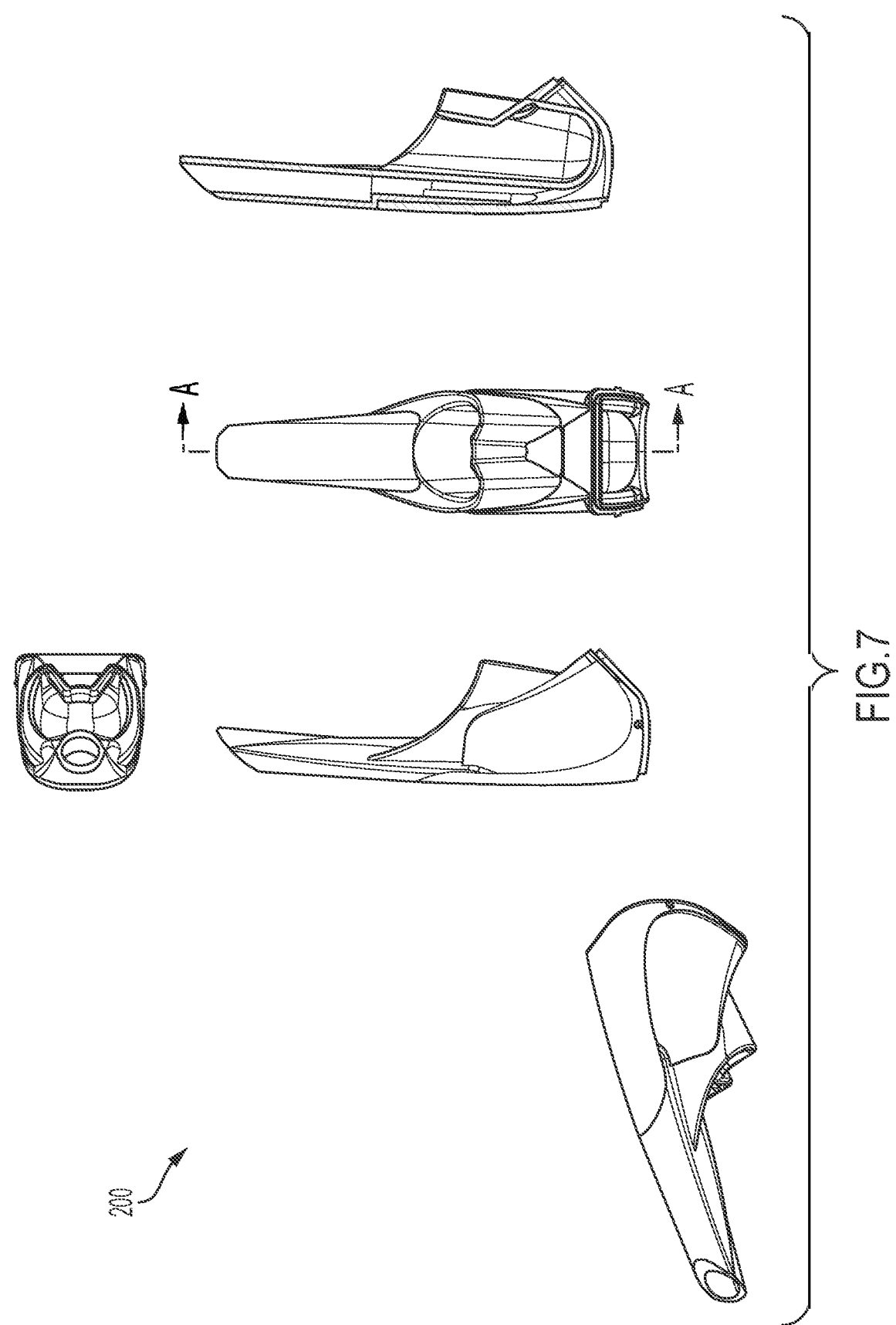
FIG. 7 is a perspective view of another example of a wearable ultrasound probe, in accordance with various embodiments.
Figure 8:
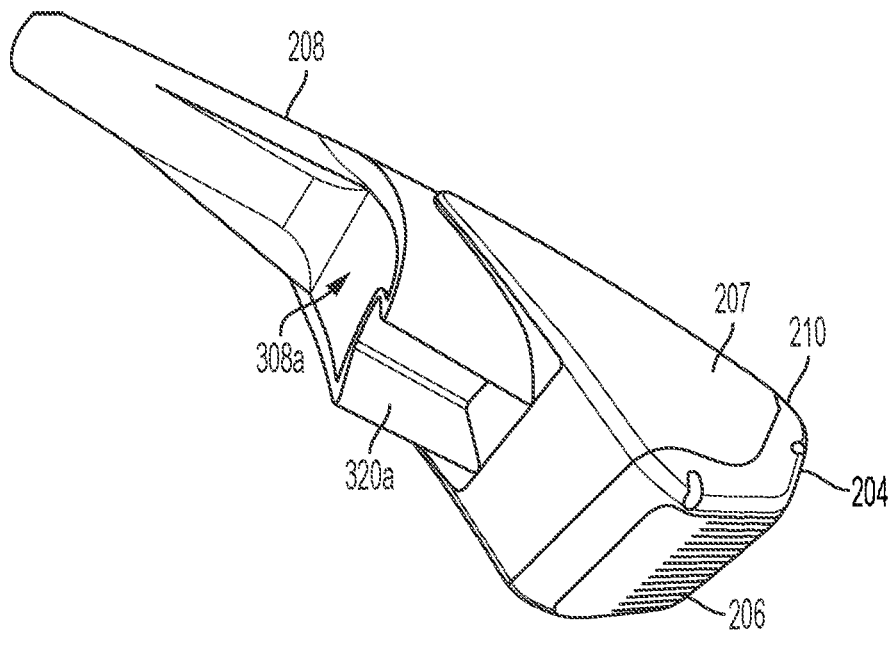
FIG. 8-8A includes two rear perspective views of two embodiments of a wearable ultrasound probe, showing two different versions of finger-receiving apertures and finger-retaining elements, in accordance with various embodiments.
Figure 8A:
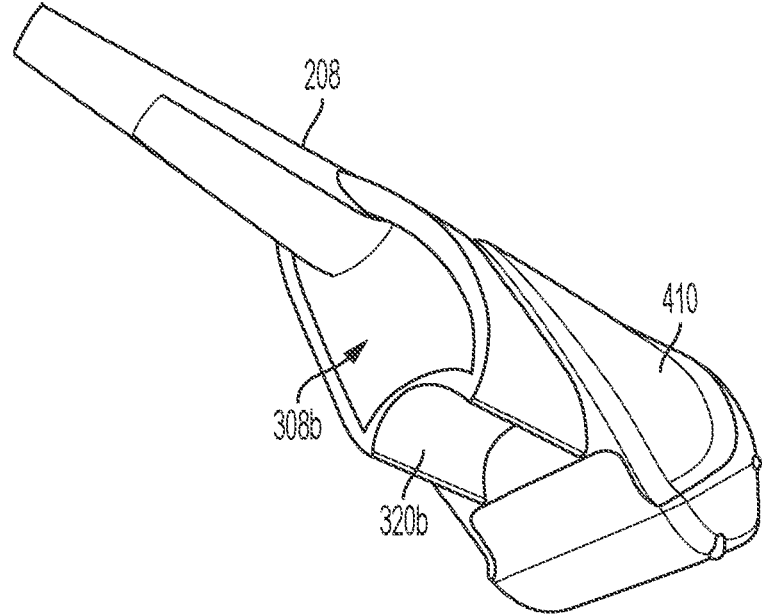

FIG. 7 includes several views of the housing of the ultrasound probe of FIGS. 1-4, all in accordance with various embodiments. FIG. 8 is two distal perspective views of various embodiments of the probes disclosed herein. As shown, the probe 200 includes a first array (e.g., the phased array) 204 disposed at the distal end of a housing, and a second array (e.g., the linear array) 206 disposed adjacent the distal end, and proximal to the first array 204. The housing includes a headshell 207, strain relief 208, and nose piece 210. The housing positions the first array 204 and second array 206 in particular spatial relationships with respect to the longitudinal axis and with respect to each other, as described above. Each array includes of an array of ultrasound elements, such as piezoelectric elements or a CMUT sensor, which convert electrical impulses into ultrasonic or acoustic energy and returning ultrasonic energy into electrical impulses which can be processed into images.

In various embodiments, the housing may also include one or more external gripping elements 410, for example that may be disposed on the left and right sides of the housing, adjacent the distal end. These gripping elements may be a softer polymer surface, or they may be an array of discrete elements formed from a softer polymer as dots or ridges, or they may be textured areas. In use, when an operator inserts an index finger into the housing, the left and right external gripping members may be positioned where the thumb and middle fingers rest, so that an operator may use the thumb and middle fingers to stabilize, rotate, and direct the probe in a desired direction/orientation to obtain a desired ultrasound image. Additionally, the external gripping elements may be used without inserting a finger into the probe, such that it may be used as a handheld probe when desired.

Figure 9:
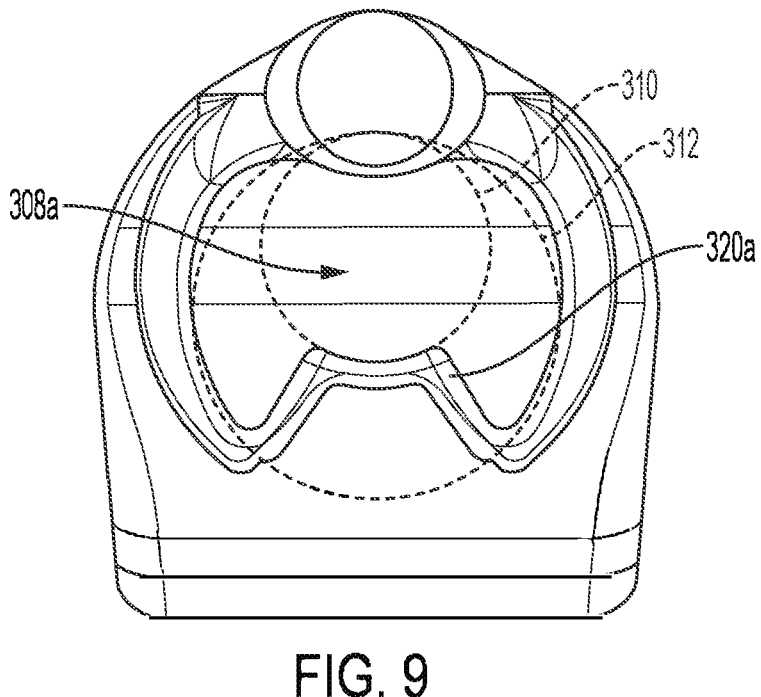
FIG. 9-9A includes cross-sectional views of the two finger-receiving apertures and finger-retaining elements of FIG. 8, in accordance with various embodiments.
Figure 9A:
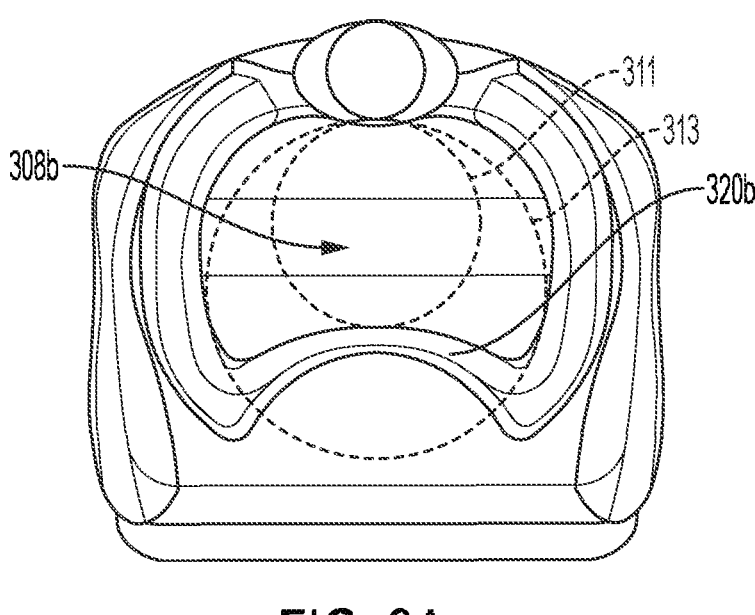

FIG. 9 includes cross-sectional views of the two finger-receiving apertures and finger-retaining elements of FIG. 8, in accordance with various embodiments. In various embodiments, the proximal end of the housing, where the operator's finger is inserted, may include a finger-retention element 320a, 320b. In some embodiments, the finger-retention element 320a, 320b may be formed from an elastomeric and/or deformable material, such that insertion of the user's finger may cause at least a portion of the finger-retention element 320a, 320b to expand or deform, thereby applying a gripping force to the finger. In various embodiments, the finger retention element may have a durometer or be made from a material having a durometer of about 30 A to 70 A, such as about 35 A to 65 A, or about 40 A to 60 A, or about 45 A to 55 A, or about 50 A. By contrast, other portions of the probe housing may be made of a harder material, such as ABS plastic, which may be about 95-115 Shore D on the hardness scale.

More specifically, in various embodiments, the finger-receiving aperture 308a, 308b may form a sleeve that includes a substantially tubular wall member formed from an elastomeric material. The sleeve may have an inner lumen sized to accommodate an average human index finger. In some embodiments, a portion of the substantially tubular wall may extend or project into the lumen to form a deformable gripping member that grips the finger. The deformable gripping member may have any of several different cross-sectional forms, such as an inward curve, arc, crease, pleat, or fold, or a more complex shape such as a combination of curves and/or folds that together form an "M" or "W" shape when viewed in cross-section. In various embodiments, insertion of a finger into the sleeve may cause the inward-facing arcuate, creased, folded, or pleated deformable gripping member to flex radially outward to accommodate the diameter of the finger. In so doing, the deformable gripping member may exert a force against the finger surface that may help retain the probe on the finger during use. As illustrated in FIG. 9, an anthropometric range of finger sizes may be accommodated by the finger-retention element 320a, 320b, from 5% (small circle 310) to 95-98% diameters (large circle 312). In various embodiments, the indented elastomeric finger-retention element 320a, 320b may distend to accommodate the large finger, yet grip the small finger. In various embodiments, the "W" shaped finger-retention element may accommodate a 95th percentile finger diameter, while the "M" shaped finger-retention element may accommodate a 98th percentile finger diameter.

Figures 13A, 13B, 13C, 14:
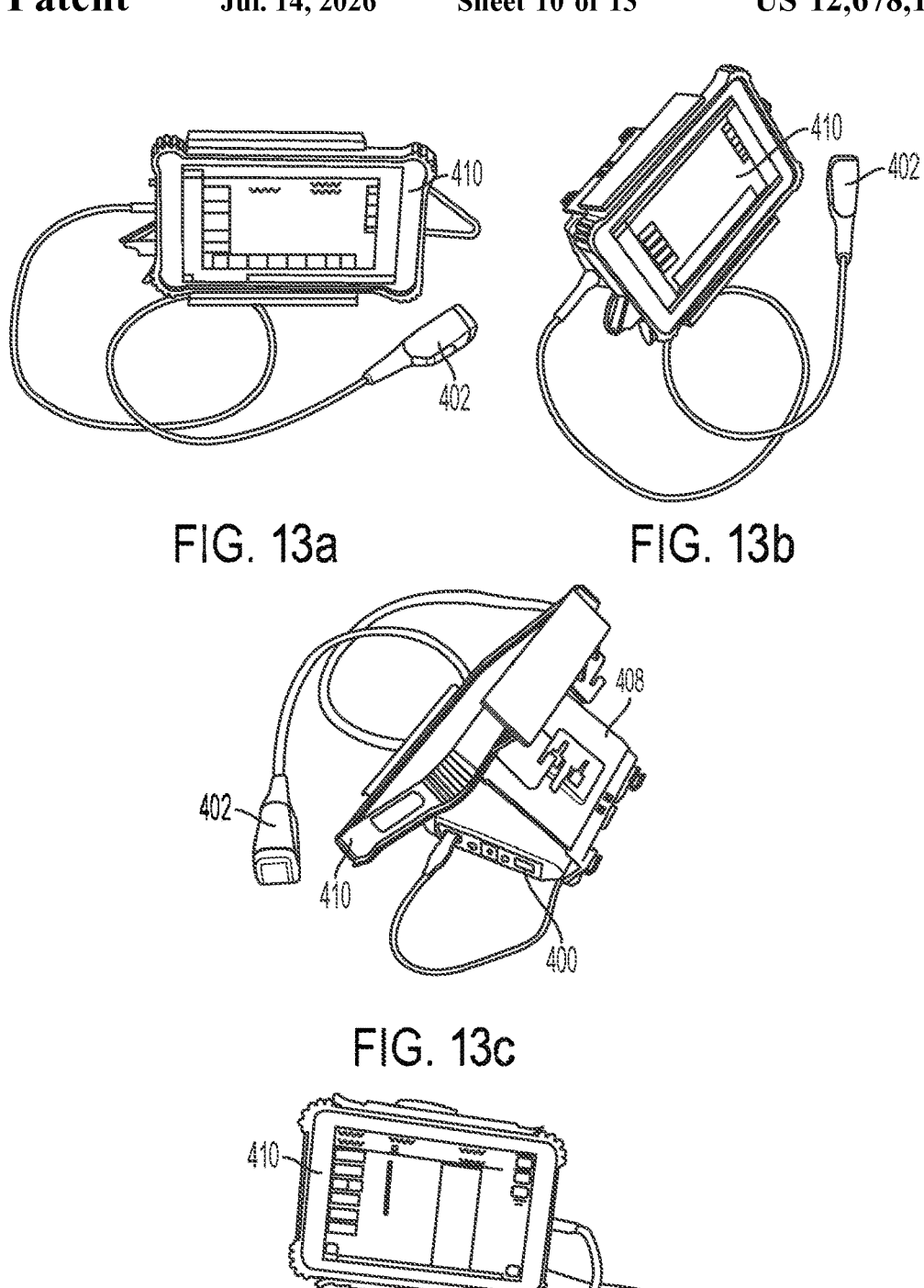
FIG. 13A-13C includes three perspective views of an ultrasound system in accordance with the various embodiments disclosed herein in which the processing component is removably affixed to the display as discussed herein.
FIG. 14 illustrates an ultrasound system in accordance with the various embodiments disclosed herein in which the processing component is integral with the display.

As shown in FIG. 13, some embodiments of an ultrasound system in accordance with the disclosure provided herein may include three components: (1) the probe 402; (2) a processing component 400 which may contain a multiplexor, user interface elements, ultrasound front end processing, a beamformer board, a battery, transducer interface board, wireless board, a heat pipe, and/or a blower fan; and (3) a tablet, mobile phone, or other wireless computing device 410 that includes back end processing capabilities and a touchscreen display, which acts as the primary user interface. In various embodiments, the system may use a USB Cable in lieu of a wireless connection.

A beamformer emits the electrical pulses which are transformed into ultrasonic energy by the probe and used to image the patient or substrate. The beamformer originates the signal, and times it in order to focus the acoustic beam that emits from the array. The beamformer determines the amplitude and frequency of the signal. The beamformer also receives the signal and demodulates, filters, detects, and compresses the signal and converts ultrasound data into pixels, or processed image information which can then be converted to a video stream and fed to the display.

Synthetic beamforming may be used in some embodiments of the system disclosed herein. Synthetic beamforming generates ultrasound images by archiving several transmit-receive events which are then coherently summed to form a synthetic beam. The inventors of the system described herein have used synthetic beam forming to generate diagnostic quality images at up to 24 cm depth at 10 frames per second with a 32 channel transmit and 16 channel receive stepped synthetic aperture.

In accordance with some embodiments of the system disclosed herein, the processing component may include may include ultrasound front end functionality, a transmit/receive switch, amplification, digitization, and beamformer, connection capability such as wi-fi, Ultra Wide Band, or USB. Additionally, the processing component may store and executes instructions supplied by the operating system that directs the performance of the system.

Figure 16:
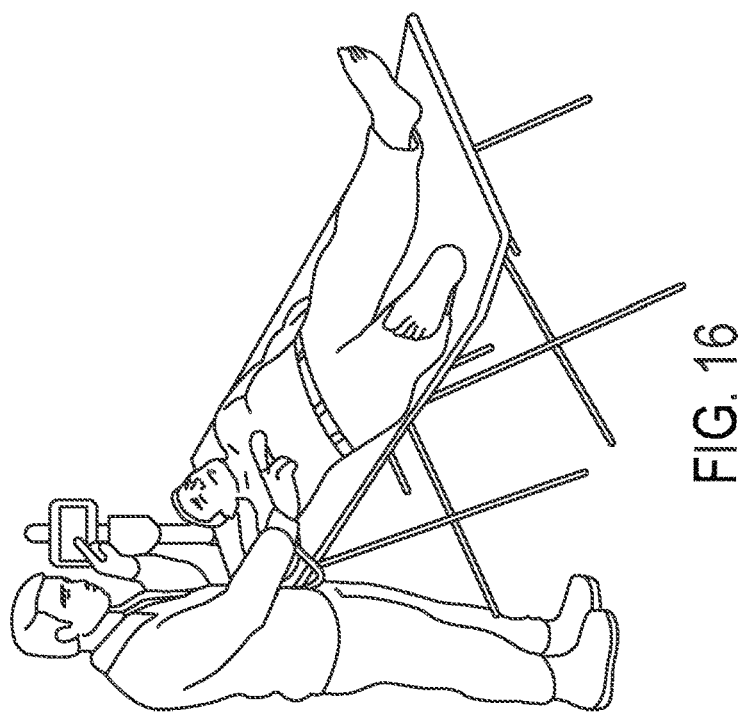
FIG. 16 illustrates an ultrasound system in accordance with the various embodiments disclosed herein wherein the processing component and display are affixed to a component of the patient's bed.
Figure 15:
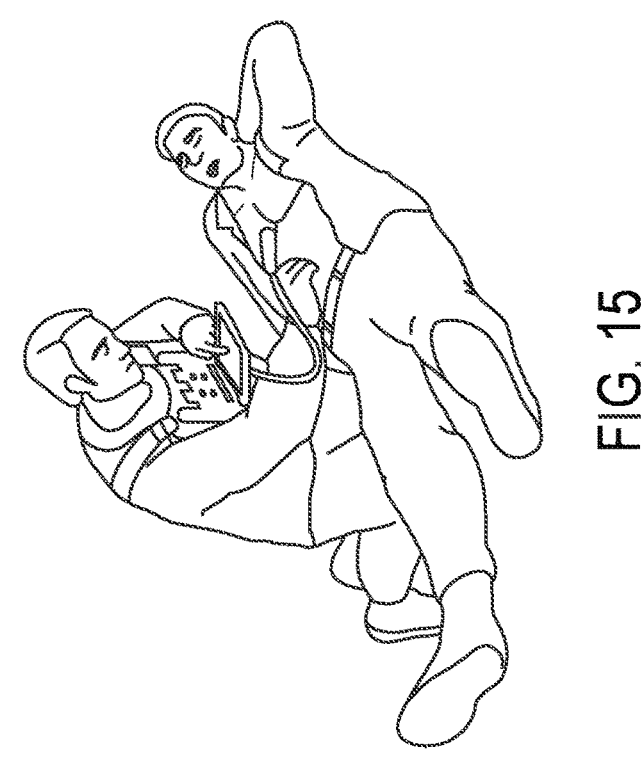
FIG. 15 illustrates an ultrasound system in accordance with the various embodiments disclosed herein wherein the processing component is affixed to the back of the display, and both are mounted to the chest of body armor.
Figure 18:
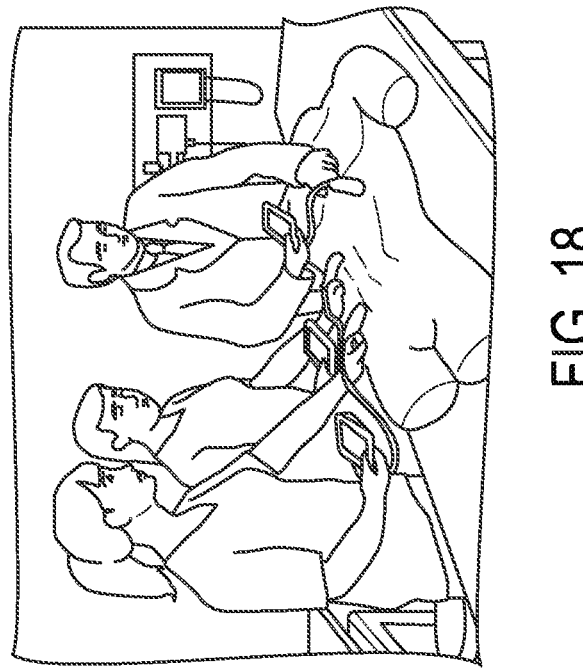
FIG. 18 illustrates the use of ultrasound systems in accordance with the various embodiments disclosed herein wherein the display is held in users' hands.
Figure 17:
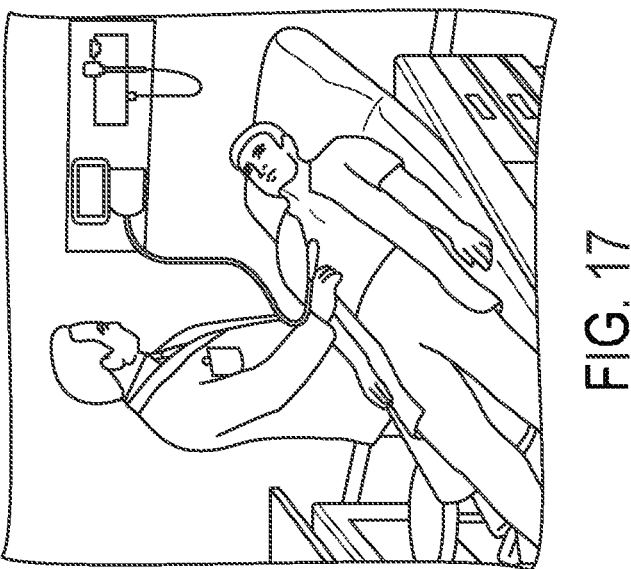
FIG. 17 illustrates an ultrasound system in accordance with the various embodiments disclosed herein wherein the processing component and display are affixed to a wall.
Figure 19:
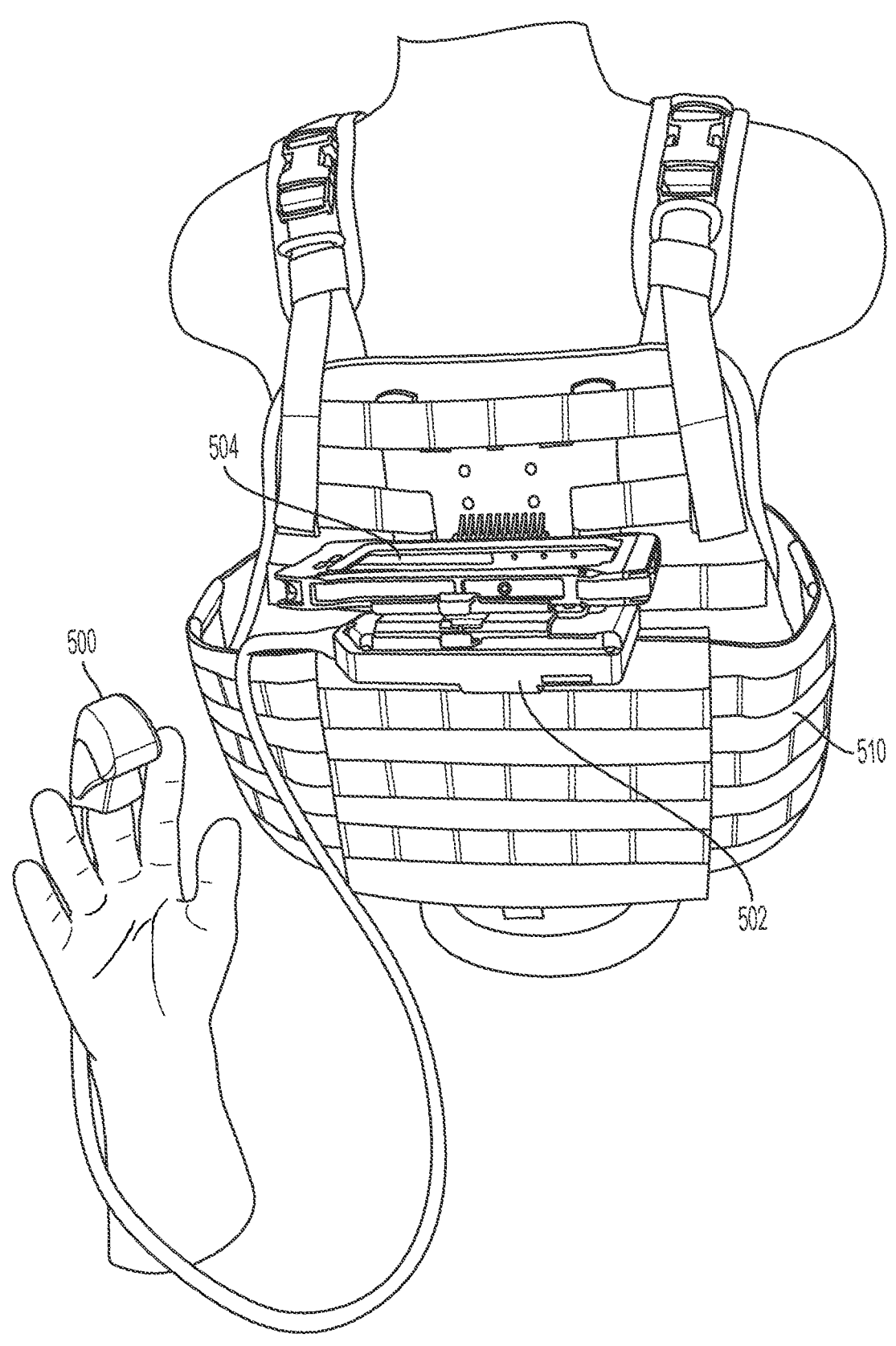
FIG. 19 illustrates an ultrasound system in accordance with the various embodiments disclosed herein wherein the processing component and display are affixed to body armor.

The processing component 400 may alternatively be mounted beneath the display, as shown in FIGS. 11a, 11b, and 11c, in which the processing component is affixed in a bracket 408 which is removably affixed to a tablet or mobile computing device 410 and positions the tablet or mobile computing device 410 where it can be seen by the operator. Alternatively, as shown in FIG. 12, the processing component may be affixed to the back of the wireless computing device or other display 410. The display and processing component may be affixed to stationary structures such as a component of a cot, gurney, or bed, as shown in FIG. 16, or a wall, as shown in FIG. 17. It can also be held by an operator as shown in FIG. 18. It may be clipped to the belt or clothing of a user (not shown). FIGS. 15 and 19 show the processing component and display attached to the body armor of a user.

In various embodiments, the ultrasound systems disclosed herein may be controlled by software that includes instructions to implement various operations recorded in non-transitory computer readable media. These instructions may make up an operating system which directs the system to perform operations associated with system set up, system control, scanning, data acquisition, beamforming, signal processing, and image creation. The operating system may include data files and data structures in addition to program instructions. The processors also may include memory consisting of hardware specially configured to store and perform program instructions such as the operating system and to record and store data and images generated by the system.

Figure 10:
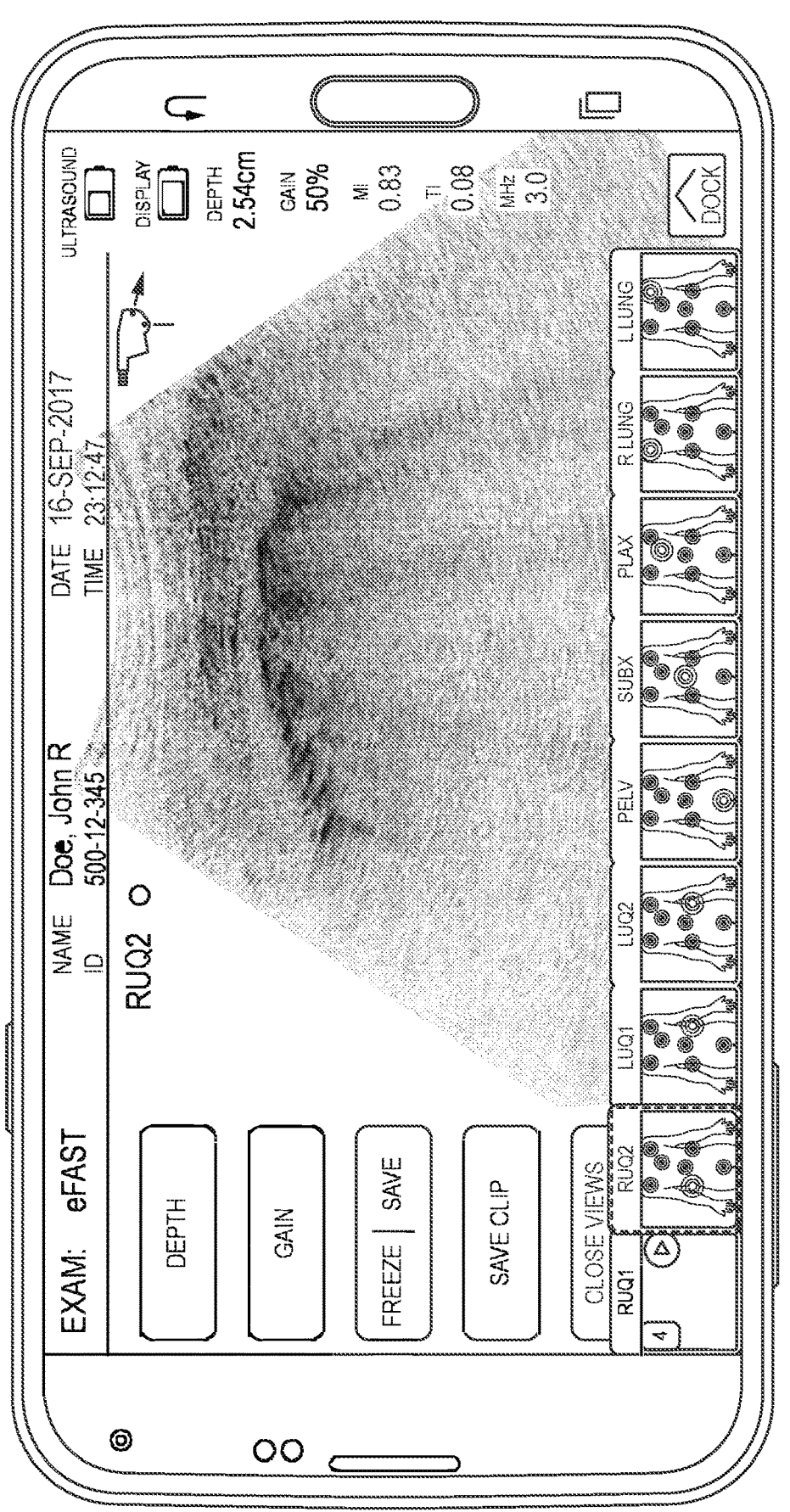
FIG. 10 illustrates one example of a graphical user interface for conducting an eFAST examination.
Figure 11:
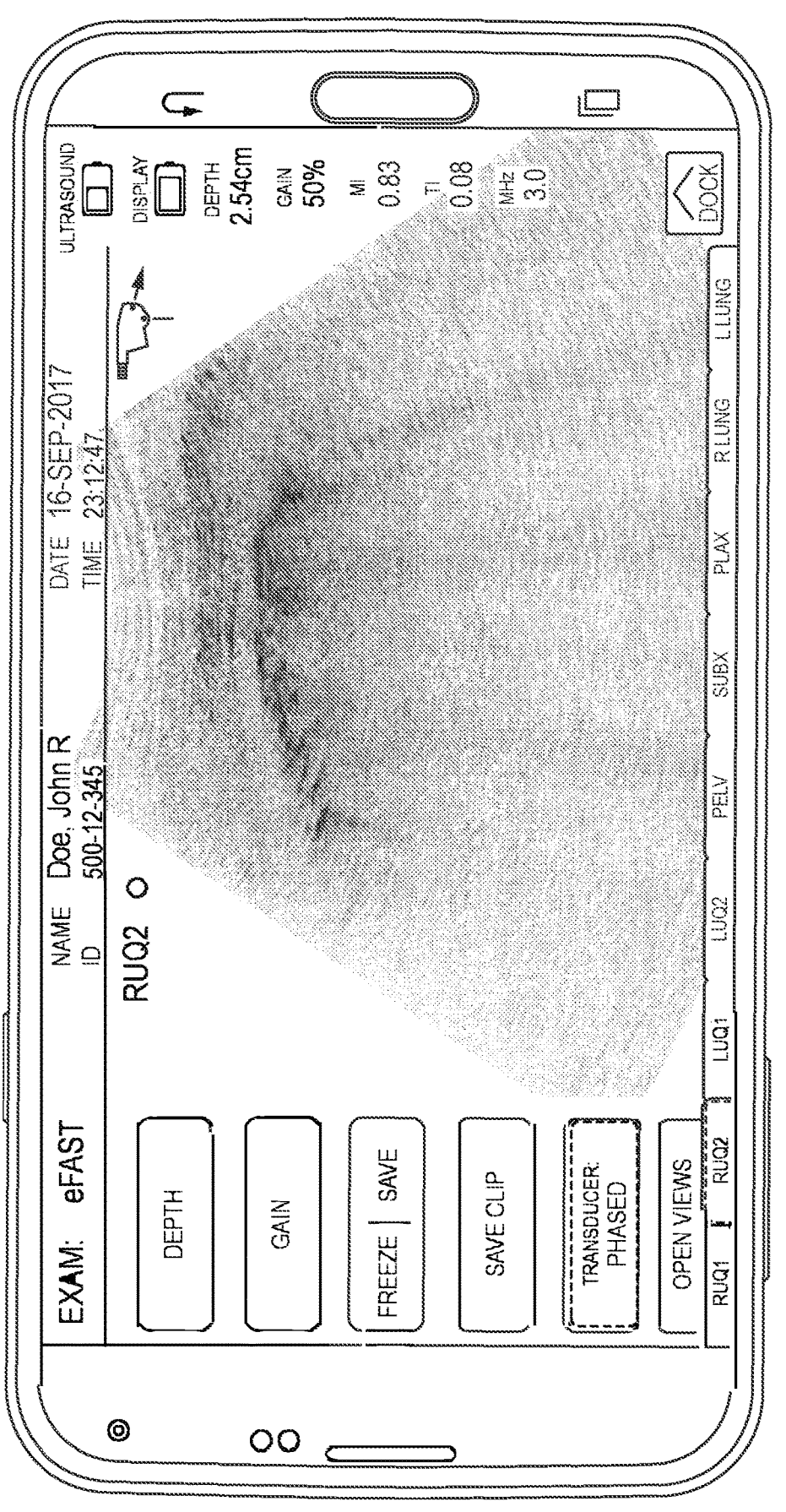
FIG. 11 illustrates one example of a graphical user interface for conducting an eFAST examination.
Figure 12:
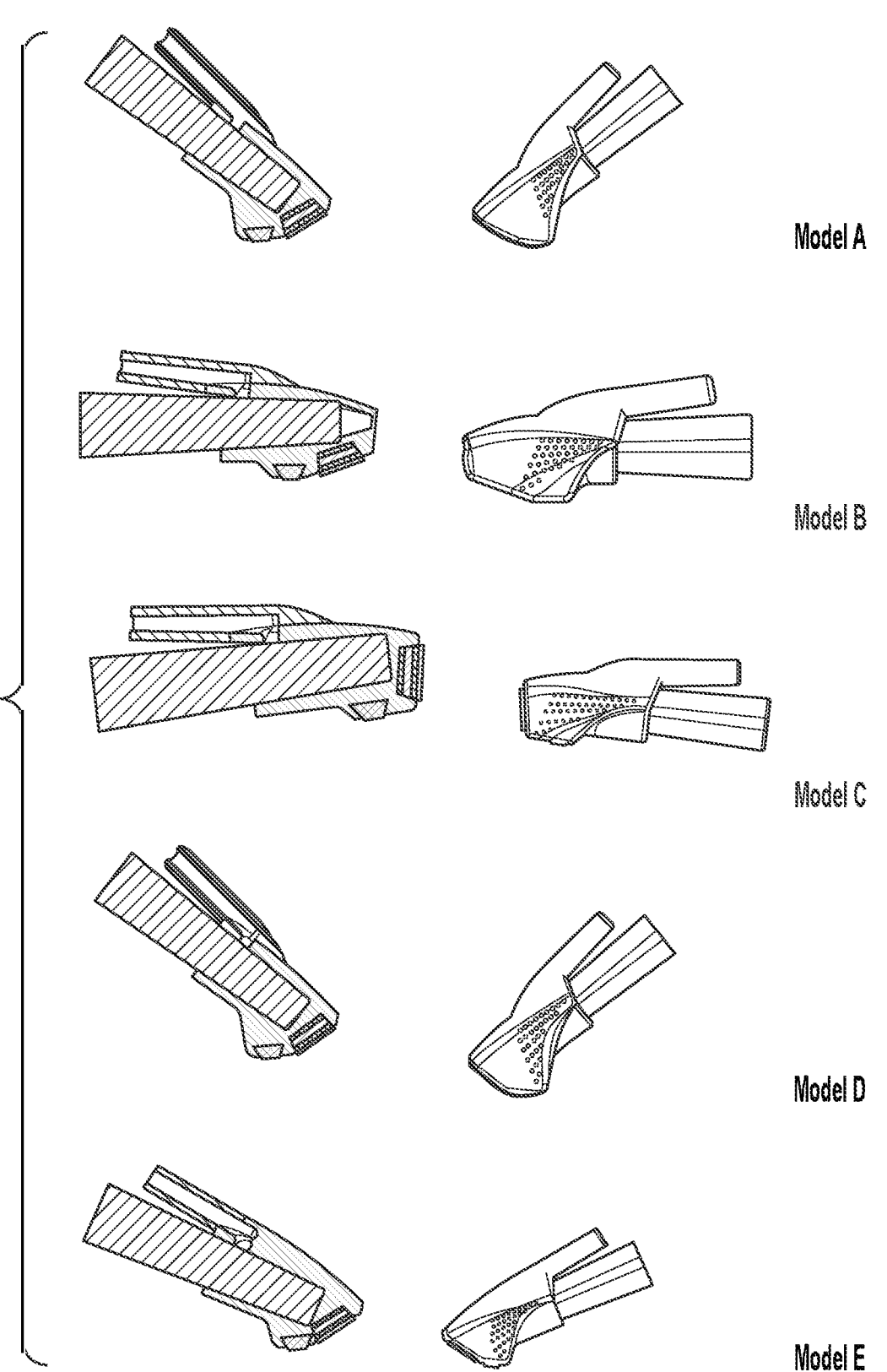
FIG. 12 illustrates a series of five probe embodiments in which the placement of arrays were varied for testing; in accordance with various embodiments.

In various embodiments, the processing component also may include an graphical user interface, certain embodiments of which are shown in FIGS. 10 and 11, which receives signals generated by user interface elements on the tablet, mobile phone, or other computing device that alters the action of the beamformer, processors, and/or other components in order to conform the performance of the system with the user input. For example, it may alter system performance in accordance with preset scanning parameters as described below.

Ultrasound scanning is subject to variable parameters, and manipulation of those parameters enables users to optimally image structures located at various depths within a substrate such as a patient's body. Ultrasound system user interfaces typically have some or all of the following user inputs: a power switch, an ability to adjust the array, an ability to adjust the gain, or brightness or vividness of the signal, an ability to optimize images, and a zoom capability. In various embodiments, a dual-array probe may be interconnected with a user interface which enables a user to change the selected array. Battery change indicators, screen brightness and contrast, and arrows to move between images are also important features. Finally, ultrasound system user interfaces typically allow users to freeze images and to save or record images or video.

Additionally, most ultrasound systems include presets, which are used to set standardized parameters for standardized scans. The extended, Focused Assessment using Sonography in Trauma (eFAST) exam is a universally accepted triage and rapid assessment tool based on a rapid ultrasound survey of key organs, internal bleeding, and heart and lung function. The FAST protocol involves serial scans: the subxiphoid four chamber view and the parasternal long axis view of cardiac anatomy; abdominal and lower thoracic views including the upper peritoneum and Morison's pouch between the liver and right kidney and the lower peritoneum posterior to the bladder in the male and the pouch of Douglas (posterior to the uterus) in the female; right coronal and intercostal oblique views in the mid-axillary line giving coronal views of the interface between the liver and kidney; left coronal and intercostal oblique views from the posterior-axillary line producing coronal views of the spleen and diaphragm; longitudinal and transverse lower pelvic views of the bladder (male/female) and uterus (female); and anterior thoracic views of the pleural interface (to access pneumothorax) through the 3-4th intercostal space and midclavicular line.

An e-FAST examination is facilitated by preset parameters most appropriate for each successive scan, e.g., gain, depth, scan plane, and other system parameters optimized for each area of the body scanned during an eFAST exam, pre-programmed into the system and categorized by scan. A user can initiate an eFAST exam, causing the system to automatically set system parameters optimized for the first scan in accordance with the first pre-set. When a user has completed that scan, the user so indicates to the system, which saves the scan and then changes system parameters so that they are optimized for the next scan in accordance with the next pre-set, and so on.

Icons that represent each scan in an e-FAST exam permit a user to indicate which scan he or she would like to perform. In response to that indication, the system is automatically configured to scan in accordance with the preset parameters associated with that scan. Preset scan parameters mean that users need not adjust individual parameters when transitioning between scans. Instead, users merely transition between preset parameters as they transition between scans. Other presets may be used within the spirit and scope of the system disclosed herein. For example, presets may be defined by the area of the body to be imaged, for example, eye, breast, spleen, bladder, etc.

Examples: Evaluation of Probe Architectures

Five probe prototypes were developed to be evaluated for ergonomic compatibility with the eFAST exam. These prototypes tested two variables: (1) the angle from the surface of the patient to perpendicular to the patient (5.5 degrees to 52 degrees); and (2) the angle between the phased array and the linear array (105 degrees to 165 degrees). All prototypes had the identical array scan plain orientations (phased array scan plane in parallel to the finger and the linear array scan plane perpendicular to the finger) and all had the phased array nearest the tip of the finger. FIG. 12 illustrates a series of cross sectional views of five probe embodiments in which the placement of the first and second arrays were varied for testing; in accordance with various embodiments. More detailed illustrations of each design are shown in the Appendix.

A total of 13 emergency medicine residents (at Madigan Army Medical Center—MAMC) and 13 medical students (at College of Osteopathic Medicine of the Pacific Northwest—COMP) participated in the study. Separate trails took place at each facility. A survey (identical for both sites) consisted of a questionnaire which the participants filled out after using both standard probes and mockups to perform a mock eFAST exam on a mannequin dummy. Each eFAST exam view (5 total) was rated, plus an overall rating was given for the standard probe and each mockup. The results from both sites are summarized in Tables 1 and 2.

TABLE 1

Sonivate Mockup surveys at MAMC
(Representative of more experienced users familiar with ultrasound)

| Evaluations | MAMC | Standard Probe | Prototype A | Prototype B | Prototype C | Prototype D | Prototype E |
|---|---|---|---|---|---|---|---|
| Excellent = 5 | Cardiac | 4.00 | 2.54 | 2.46 | 3.23 | 3.31 | 2.92 |
| Very Good = 4 | RUQ | 4.38 | 2.77 | 2.85 | 3.46 | 3.62 | 3.31 |
| Good = 3 | Pelvic | 4.54 | 3.54 | 3.46 | 3.92 | 4.08 | 3.85 |
| Poor = 2 | LUQ | 4.15 | 3.69 | 3.54 | 4.00 | 4.15 | 4.00 |
| Very Poor = 1 | Pulmonary | 4.69 | 3.77 | 3.69 | 3.85 | 4.00 | 3.88 |
|  | Overall | 4.46 | 3.08 | 2.98 | 3.74 | 3.81 | 3.54 |

TABLE 2

Sonivate Mockup surveys at COMP
(Representative of less advanced ultrasound users)

| Evaluations | COMP | Standard Probe | Prototype A | Prototype B | Prototype C | Prototype D | Prototype E |
|---|---|---|---|---|---|---|---|
| Excellent = 5 | Cardiac | 3.62 | 3.00 | 3.00 | 3.54 | 3.38 | 3.31 |
| Very Good = 4 | RUQ | 3.92 | 3.62 | 3.69 | 4.15 | 3.85 | 3.54 |
| Good = 3 | Pelvic | 3.92 | 3.62 | 3.77 | 4.15 | 4.00 | 3.85 |

TABLE 2-continued

Sonivate Mockup surveys at COMP
(Representative of less advanced ultrasound users)

| Evaluations | COMP | Standard Probe | Prototype A | Prototype B | Prototype C | Prototype D | Prototype E |
|---|---|---|---|---|---|---|---|
| Poor = 2 | LUQ | 3.85 | 3.62 | 3.69 | 4.08 | 4.00 | 3.69 |
| Very Poor = 1 | Pulmonary | 3.54 | 3.69 | 3.31 | 3.62 | 4.08 | 3.77 |
| | Overall | 3.73 | 3.39 | 3.60 | 3.84 | 3.64 | 3.74 |
| Overall average between both groups | | 4.10 | 3.23 | 3.29 | 3.79 | 3.72 | 3.64 |

Overall, Prototype C was rated the highest (average of 3.8) by both the students and residents and was most chosen by the residents when directly asked. Prototype C was also rated the best for time to complete the eFAST exam.

The cardiac (subxiphoid) view was rated overall the lowest for the finger probes. Although the standard probe also had its lowest rating for the cardiac view, there appears to be a significant issue consistent across all variants of the finger probe. Mockups C and D, with the array primarily frontal, had the highest ratings among the mockups for this view among the more experienced users.

Comparing the standard probe to the wearable probe is heavily dependent upon "familiarity." The inexperienced user prefers the wearable form factor because it is easy to use, intuitive, etc., while the experienced user prefers the standard hand-held probe. The standard probe is very familiar to the experienced user and thus does not present a problem to be solved. The field medic will not be a trained user.

The most important attribute appears to be the angle of the phased array relative to the finger plane (horizontal axis). In both C and D the array was primarily "frontal" with an offset of only 15 degrees from the perpendicular face of the probe. The frontal aspect was important for allowing the probe to be placed with some pressure into the patient and also allowed greater scanning freedom of movement.

The differentiation of the two arrays is important but appears to be less important than the frontal orientation of the phased array. Prototypes C & D had the angle between the arrays at 105 degrees and 152 degrees, respectively (less angle indicates greater scan separation). Prototypes A, B & E were viewed as having insufficient angle differentiations i.e. 165 degrees. Differentiation between arrays was stated verbally to be important by several users as the speed in which the exam is conducted leaves no time for confusion (the user needs to "lock in" by tactile feel which array is being used).

The MAMC doctors indicated a preference that the scan planes point in the same direction (relative to the finger) to make the probe more intuitive and to reduce confusion of orientation when switching between arrays). This would also make the left and right upper quadrant views more comfortable while standing adjacent to the patient. The stated preference was to have both scan planes be perpendicular/transverse to the finger.

While not intentionally studied, the small forward footprint of probe C (due to the large degree of separation between arrays and the frontal angle of the probe) was seen as an advantage. This made the probe seem familiar to experienced ultrasound users, a potential advantage, with no seeming disadvantage for less experienced users. Given the similar ratings for C & D, it was interesting that C, perceived the best, was only 5.5 degrees; whereas, D was 52 degrees and received similar but slightly lower overall ratings.

(However, this may be due to confounding factors such as the small footprint and the identical forward angle of both probes). In both variants, it is easy to push hard on the phased array because of the frontal orientation. The comments suggest one design or the other; a compromise in the middle (i.e. Prototype E) may not be appropriate as noted and rated (i.e. 3.54) by the Army doctors. (Given that C is a lower profile, it also has the advantage for use with body armor and shock blankets.)

All finger probe variants had consistently low ratings for the cardiac view from both the students and doctors. The doctors' ratings were particularly low across the prototypes (i.e. 2.5 to 3.3). Alternative cardiac views such as the parasternal four-chamber view may be easier to obtain with the finger probe phased array.

There appears to be a clear advantage for Prototypes C & D for the Pelvic and LUO views. Also Prototype D is perceived as being very good for the pulmonary/pneumothorax view by the Army doctors (likely because of the greater finger angle relative to the linear array, offering a more comfortable hand position). The grips on each of the prototypes were viewed positively. Participants even could tell that "E" had fewer raised dots due to its design. There is a positive aspect to the design when the clinician has permission to hold or use the finger inserted.

It can be seen that the frontal angle of the phased array relative to the finger orientation is the same for both probes C and D. Since the array angle separation varied significantly, yet both probes received similar scores, the array orientation may be less critical, at least when separated beyond a critical angle. A final design will keep the frontal orientation of the phased array relative to the finger angle and place the linear scan angle somewhere between C and D versions. Version D was rated higher for the pneumothorax view, the only eFAST scan that uses the linear array. However D presents a larger footprint and less array separation, which detracted from the other views. As most eFAST exams are performed with the phased array, designs should be biased toward the C design, but slight angle increases of the linear probe toward the D design may improve comfort for the pneumothorax view without detracting from the other views.

For example, the probes illustrated in FIGS. 1-8 represent intermediates between probes C and D. One embodiment representing an optimization of these results is depicted in FIGS. 1-4. FIGS. 1-4 illustrate a preferred orientation of the first and second arrays, with the longitudinal axis labelled "0-180," the angle of the first array relative to the longitudinal axis labelled "a", and the angle of the second array relative to the longitudinal axis labelled "b".

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A wearable ultrasound probe comprising:
a housing having a top side and a bottom side, a proximal end and a distal end, and a longitudinal axis extending therebetween, wherein the proximal end comprises a finger-receiving aperture that is configured to form a sleeve including a tubular wall member formed from an elastomeric material and defining an inner lumen, a bottom side of the tubular wall member configured to extend or project into the inner lumen to form a deformable gripping member for gripping a finger, and wherein the extension or projection of the bottom side of the tubular wall member into the inner lumen is configured to retain relatively small diameter fingers while the extension or projection of the bottom side of the tubular wall member is configured to distend outward from the inner lumen to accommodate relatively large diameter fingers; and
at least one ultrasound array disposed at the distal end, wherein the at least one ultrasound array is a phased array or a linear array.

2. The wearable ultrasound probe of claim 1, wherein the at least one ultrasound array comprises a first ultrasound array and a second ultrasound array, wherein the second ultrasound array is disposed adjacent to the distal end and is proximal to the first ultrasound array.

3. The wearable ultrasound probe of claim 2, wherein the second ultrasound array is angled 105-155 degrees from the first ultrasound array such that only one of the first ultrasound array or the second ultrasound array is positionable against a patient and usable at one time.

4. The wearable ultrasound probe of claim 1, wherein the at least one ultrasound array is oriented transverse to the longitudinal axis.

5. The wearable ultrasound probe of claim 1, wherein the finger-receiving aperture comprises a finger-retention element.

6. The wearable ultrasound probe of claim 1, wherein the housing further comprises a left side and a right side, and wherein the left and right sides each comprises a gripping element.

7. The wearable ultrasound probe of claim 6, wherein the gripping elements are positioned adjacent to the distal end.

8. The wearable ultrasound probe of claim 1, further comprising a strain relief section that extends from the proximal end of the housing.

9. The wearable ultrasound probe of claim 1, wherein a cross-section of the tubular wall member includes at least one of an inward curve, an arc, a crease, a pleat, or a fold.

10. A wearable ultrasound probe comprising:
a housing having a dorsal side and a palmar side, a proximal end and a distal end, and a longitudinal axis extending therebetween, wherein the proximal end comprises a finger-receiving aperture that is configured to form a sleeve including a tubular wall member formed from an elastomeric material and defining an inner lumen, a portion of the tubular wall member configured to extend or project into the inner lumen to form a deformable gripping member for gripping a finger, and wherein the extension or projection of the tubular wall member into the inner lumen is configured to retain relatively small diameter fingers while the extension or projection of the tubular wall member is configured to distend outward from the inner lumen to accommodate relatively large diameter fingers; and
an ultrasound array disposed at the distal end or adjacent to the distal end.

11. The wearable ultrasound probe of claim 10, wherein the ultrasound array is a phased array configured for imaging in a non-near field over a wide field of view.

12. The wearable ultrasound probe of claim 10, wherein the ultrasound array is a linear array configured for imaging in a near field over a narrow field of view.

13. The wearable ultrasound probe of claim 10, wherein the ultrasound array is oriented transverse to the longitudinal axis.

14. The wearable ultrasound probe of claim 10, wherein the finger-receiving aperture comprises a finger-retention element.

15. The wearable ultrasound probe of claim 10, wherein the housing further comprises a left side and a right side, and wherein the left and right sides each comprises a gripping element.

16. The wearable ultrasound probe of claim 15, wherein the gripping elements are positioned adjacent to the distal end.

17. The wearable ultrasound probe of claim 10, further comprising a strain relief section that extends from the proximal end of the housing.

18. The wearable ultrasound probe of claim 17, wherein the strain relief section is configured to enclose a portion of a cable for electrically connecting to the ultrasound array.

19. The wearable ultrasound probe of claim 17, wherein the strain relief section is configured to rest on a dorsal surface of the finger when the finger is placed into the finger-receiving aperture.

20. The wearable ultrasound probe of claim 10, wherein a cross-section of the tubular wall member includes at least one of an inward curve, an arc, a crease, a pleat, or a fold.

* * * * *